US00PP37543P2

(12) United States Plant Patent
Berry

(10) Patent No.: US PP37,543 P2
(45) Date of Patent: Jul. 28, 2026

(54) ***HIBISCUS* PLANT NAMED 'JBG 15010'**

(50) Latin Name: *Hibiscus rosa-sinensis*
Varietal Denomination: JBG 15010

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 19/217,574

(22) Filed: May 23, 2025

(51) Int. Cl.
*A01H 5/00* (2018.01)
*A01H 6/60* (2018.01)

(52) U.S. Cl.
USPC ..... Plt./257

(58) Field of Classification Search
USPC ..... Plt./226, 257
See application file for complete search history.

(56) References Cited

U.S. PATENT DOCUMENTS

| | | | | |
|---|---|---|---|---|
| PP31,854 | P3 | 6/2020 | Berry | |
| PP32,773 | P2 * | 1/2021 | Berry | A01H 6/608 Plt./257 |
| PP34,662 | P2 * | 10/2022 | Berry | Plt./257 |
| PP34,663 | P2 * | 10/2022 | Berry | Plt./257 |
| PP34,664 | P2 * | 10/2022 | Berry | A01H 5/02 Plt./257 |

* cited by examiner

*Primary Examiner* — Karen M Redden
(74) *Attorney, Agent, or Firm* — The Webb Law Firm

(57) ABSTRACT

A new and distinct *Hibiscus* plant having large, gold-colored flowers with a prominent eye and slightly ruffled petals.

2 Drawing Sheets

Botanical classification: *Hibiscus rosa-sinensis.*
Varietal denomination: 'JBG 15010'.

BACKGROUND OF THE INVENTION

The present invention comprises a new and distinct *Hibiscus* plant having the varietal name 'JBG 15010'. The new variety is the result of a planned breeding program in Grand Saline, Texas, with the purposes of developing *Hibiscus rosa-sinensis* plants that exhibit whitefly and bacterial and fungal leaf spot resistance, propagation and production efficiencies, durable and exotic flowers, and abundant flowering. The parentage of 'JBG 15010' is unknown. 'JBG 15010' was discovered in February 2015, and was first asexually reproduced, by cuttings, in Grand Saline Texas in March 2016. 'JBG 15010' has been trial and field tested and has been found to retain its distinctive characteristics and remain true to type through successive propagations. The present invention has not been evaluated under all possible environmental conditions. However, it has been found to thrive in production and adapt well to the environment in Homestead, Florida and Los Fresnos, Texas. The phenotype may vary with variations in environment without a change in the genotype of the plant.

When 'JBG 15010' is compared to *Hibiscus rosa-sinensis* variety 'JBG 14003', described in U.S. Plant Pat. No. 31,854, both varieties have concentric color patterns with an eye, and flowers presented in an upright form and having an orange color. However, 'JBG 15010' differs from 'JBG 14003' in foliage shape and has darker green foliage and a higher resistance to bacterial leaf spot than 'JBG 14003'.

The following traits distinguish 'JBG 15010' as a new and distinct cultivar from other *Hibiscus* varieties known to the breeder:

1. Large size of the flowers;
2. Large size of the foliage;
3. Robustness and growth, resulting in a large plant;
4. Flower color is a vibrant golden color with a dark maroon eye and pink edging around the eye; and
4. Slightly ruffled petals.

DESCRIPTION OF THE DRAWINGS

The accompanying photographic images illustrate the new variety at approximately eleven months of age, with the colors being as nearly true as is possible with color illustrations of this type.

DESCRIPTION OF THE PLANT

Figure 1:
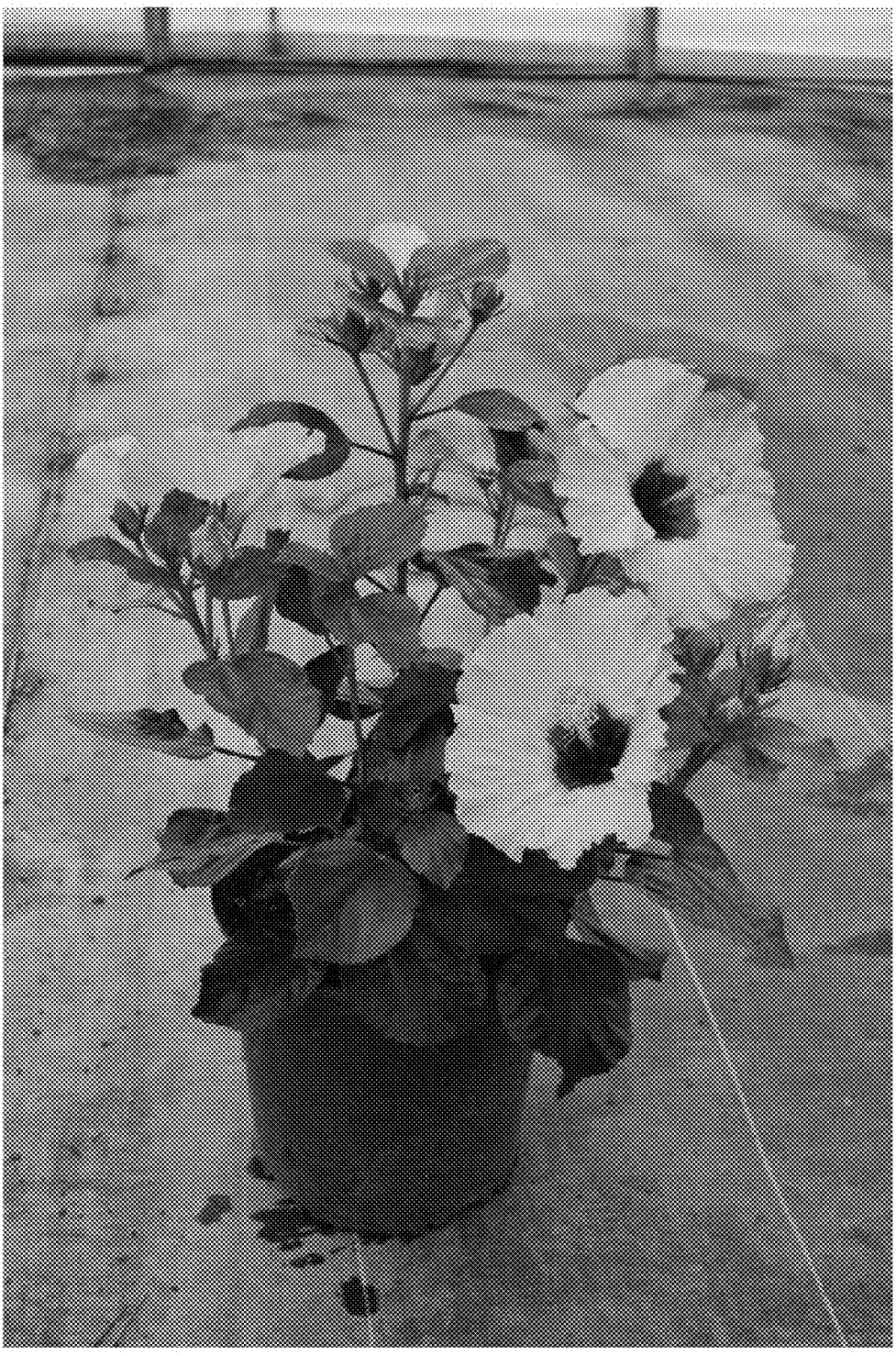
FIG. 1 illustrates an entire plant of the new variety.
Figure 2:
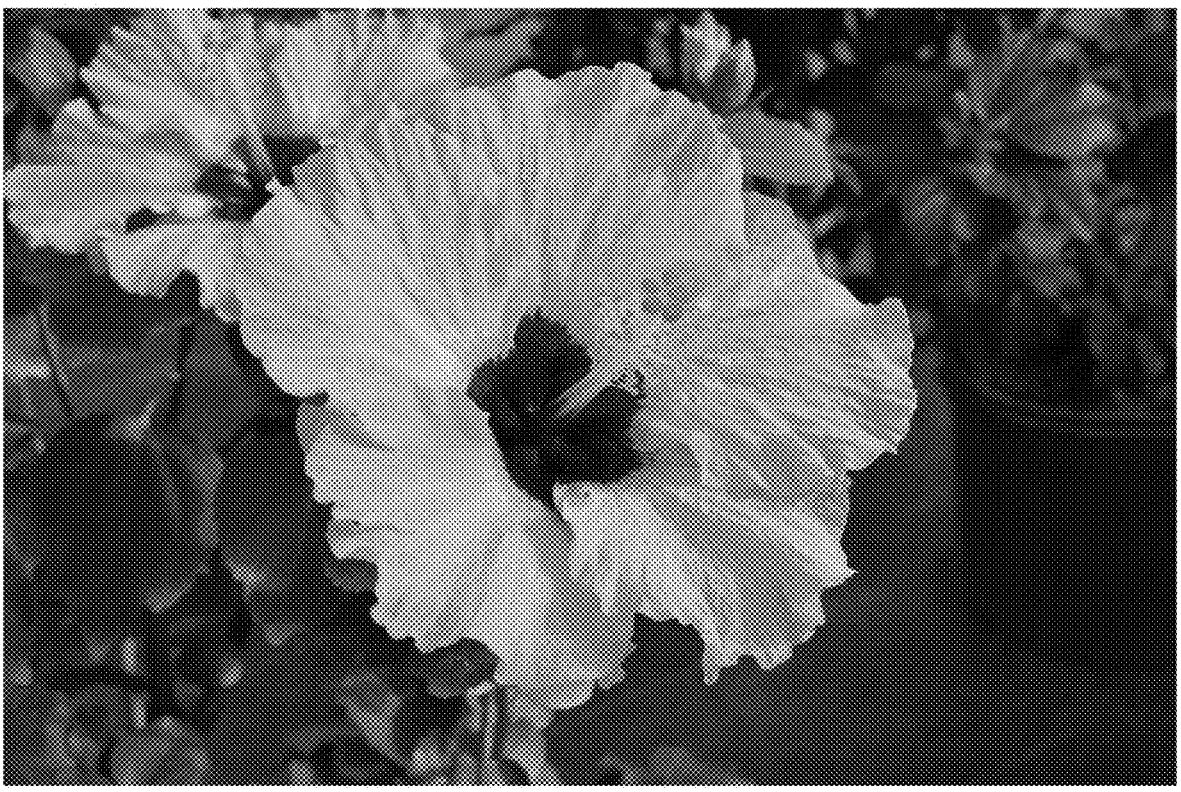
FIG. 2 illustrates a close-up view of a flower of the new variety.

The following detailed description sets forth the characteristics of the new variety. The plants were grown in 2-gallon containers in a heated greenhouse with a minimum temperature of approximately 13° C. and about 30% light shade in the summer months. The color readings and measurements were taken indoors under fluorescent lights with natural light from a window nearby on approximately eight-month-old plants. Color references are primarily to The 1995 R.H.S. Colour Chart of The Royal Horticultural Society of London, 3$^{rd}$ Edition, except where general color terms are used.

PLANT

Time to initiate roots: About 12 days at an average of 24° C.

Time to develop roots: About 50 days at an average of 21-24° C.

Time to produce a finished flowering plant from a rooted cutting: About 12-16 weeks in a 1-gallon container.

Specific disease/pest resistance: Resistance to whitefly (*Trialeurodes vaporariorum*) and bacterial leaf spot (*Pseudomonas* spp.).

Heat/cold tolerance: Thrives above 13° C., but expires at temperatures of 0° C. and below.

Drought tolerance: Moderate to none.

Plant:

*Type*.—Tropical, ornamental shrub.

*Habit*.—Upright, rounded.

*Height*.—45.7 cm from the top of the pot to the top of the plant.

*Spread*.—58.4 cm.

*Vigor*.—High.

*Rooting*.—Coarse and well-branched.

Stem:

*Number per plant*.—20.

*Length*.—24.1-37.1 cm.

*Texture*.—Immature: Slightly textured. Mature: Coarse with upright edges.

*Strength*.—Firm.

*Branch number*.—16.

*Internode length*.—1.5-1.9 cm.

*Color*.—Immature: 144A. Mature: 199B.

*Stipules*.—Number per node: 2. Shape: Spinose. Length: 13 mm. Width: 2 mm. Surface texture: Smooth. Apex: Acute. Base: Linear. Margin: Entire. Color: 143A.

Foliage:

*Arrangement*.—Alternate.

*Size of leaf*.—Length: 9.7 cm. Width: 7.9 cm.

*Shape of leaf* (*generally*).—Cordate.

*Shape of apex*.—Acute.

*Shape of base*.—Rounded.

*Texture*.—Upper surface: Smooth, with a slight texture from venation. Lower surface: Slightly coarse from venation.

*Margin type*.—Crenate.

*Color*.—Young leaves: Upper surface: 141A. Lower surface: 137A. Mature leaves: Upper surface: 135A. Lower surface: 146A.

*Veins*.—Venation type: Palmate. Color: Upper surface: 137B. Lower surface: 143A.

*Petiole*.—Length: 28 mm. Diameter: 4.0 mm. Texture: Mostly smooth. Color: 143C.

FLOWERS

Buds (described at approximately 2 days from opening):

*Shape*.—Acute.

*Diameter*.—1.9 cm.

*Length*.—4.1 cm.

*Color*.—152A.

Natural flowering season: Year-round in Grand Saline, Texas.

Flower type and habit: Single with slightly overlapping petals.

Fragrance: None.

Flowers:

*Number per stem*.—1.

*Overall depth*.—3.8 cm.

*Overall diameter*.—16.5 cm.

*Shape*.—Rotate.

*Lastingness*.—2-3 days on the plant.

*Petals*.—Number: 5. Arrangement: Simple. Length: 9.5 cm. Width: 8.9 cm. Shape: Ovate. Apex: Obtuse. Base: Acute. Margin: Entire. Texture/appearance: Upper surface: Smooth. Lower surface: Slightly textured with hair-like extensions. Color: When opening: Upper surface: 169D at the end of petal, 55B edging around the eye, 34A eye color. Lower surface: 163D at top left of petal, 179C at top right of petal, and 201D at very bottom of petal. Fully opened: Upper surface: 153D at end of petal, 38A edging around eye, 59A eye color. Lower surface: 161B at the end of the petal and 8D on lowest part of petal.

*Calyx*.—Form: Fused. Overall length: 3.1 cm. Overall diameter: 2.5 cm. Sepals/calyx lobes: Number: 5. Shape: Lanceolate. Apex: Acute. Margin: Entire. Texture: Slightly textured with tiny bumps. Color: Outer surface: 144A. Inner surface: 138B.

*Epicalyx*.—Length: 2.2 cm. Width: 0.5 cm. Texture: Inside is smooth and outside is coarse. Color: 144A. Sepal-like bracts: Not present.

*Bracts*.—Not present.

*Peduncle*.—Length: 5.0 mm. Diameter: 5.0 mm. Strength: Stiffly firm. Angle: Acute. Texture: Slightly textured. Color: 143A.

Reproductive organs:

*Gynoecium*.—Pistils: Number: 1. Length: 8.4 cm. Stigma: Number: 5. Shape: Round. Length: 12.0 mm. Diameter: 4.0 mm. Color: 28A. Style: Length: 7.0 mm. Width: 1.0 mm. Color: 14D. Ovary: Shape: Ovate. Length: 9.0 mm. Width: 7.0 mm. Color: 154D.

*Androecium*.—Stamens: Number: 105. Position: Below the stigma on the style. Anther: Shape: U-shaped. Diameter: 1.0 mm. Color: 13C. Filament: Length: 6.0 mm. Width: 1.0 mm. Color: 166B. Pollen: Color: 17B. Amount (generally): Moderate.

SEEDS

Seeds: None produced.

I claim:

1. A new and distinct variety of *Hibiscus* plant named 'JBG 15010', substantially as illustrated and described herein.

* * * * *